US008367818B2

(12) United States Patent
Yoshida et al.

(10) Patent No.: US 8,367,818 B2
(45) Date of Patent: *Feb. 5, 2013

(54) LOW MOLECULAR WEIGHT HYALURONIC ACID AND/OR SALT THEREOF, AND COSMETIC PREPARATION, PHARMACEUTICAL COMPOSITION, AND FOOD COMPOSITION EACH USING SAME

(75) Inventors: Takushi Yoshida, Tokyo (JP); Katsue Takizawa, Saitama (JP)

(73) Assignee: Q.P. Corporation (JP)

( * ) Notice: Subject to any disclaimer, the term of this patent is extended or adjusted under 35 U.S.C. 154(b) by 658 days.

This patent is subject to a terminal disclaimer.

(21) Appl. No.: 12/224,272

(22) PCT Filed: Feb. 21, 2007

(86) PCT No.: PCT/JP2007/053183
§ 371 (c)(1),
(2), (4) Date: Dec. 22, 2008

(87) PCT Pub. No.: WO2007/099830
PCT Pub. Date: Sep. 7, 2007

(65) Prior Publication Data
US 2009/0312282 A1 Dec. 17, 2009

(30) Foreign Application Priority Data
Feb. 24, 2006 (JP) ................. 2006-048876

(51) Int. Cl.
*C07H 5/04* (2006.01)
*C07H 5/06* (2006.01)
(52) U.S. Cl. ..................................... 536/55.1
(58) Field of Classification Search .................. None
See application file for complete search history.

(56) References Cited

U.S. PATENT DOCUMENTS

| 5,605,891 | A | 2/1997 | Prino et al. |
| 6,018,035 | A | 1/2000 | Hai et al. |
| 6,020,484 | A | 2/2000 | Callegaro et al. |
| 2005/0090661 | A1 | 4/2005 | Asari et al. |
| 2006/0135439 | A1 | 6/2006 | Kato et al. |

FOREIGN PATENT DOCUMENTS

| EP | 0 889 055 | 1/1999 |
| GB | 2 249 315 | 5/1992 |
| JP | 62-292710 | 12/1987 |
| JP | 63-057602 | 3/1988 |
| JP | 63-150209 | 6/1988 |
| JP | 63-150210 | 6/1988 |
| JP | 63-270701 | 11/1988 |
| JP | 63-301826 | 12/1988 |
| JP | 63 301826 | 12/1988 |
| JP | 1 266102 | 10/1989 |
| JP | 1-266102 | 10/1989 |
| JP | 01-266102 | 10/1989 |
| JP | 04-158796 | 6/1992 |
| JP | 04-505774 | 10/1992 |
| JP | 05-111367 | 5/1993 |
| JP | 05-255045 | 10/1993 |
| JP | 6-157322 | 6/1994 |
| JP | 06-157322 | 6/1994 |
| JP | 06-157604 | 6/1994 |
| JP | 09-208420 | 8/1997 |
| JP | 10-195107 | 7/1998 |
| JP | 11-124401 | 5/1999 |
| JP | 2000-502141 | 2/2000 |
| JP | 2000-095660 | 4/2000 |
| JP | 2000-102362 | 4/2000 |
| JP | 2001-81103 | 3/2001 |
| JP | 2001-081103 | 3/2001 |
| JP | 2001-270829 | 10/2001 |
| JP | 2002-145750 | 5/2002 |
| JP | 2004-043645 | 2/2004 |
| JP | 2004-337151 | 12/2004 |
| JP | 2005-110675 | 4/2005 |
| JP | 2006-036666 | 2/2006 |
| JP | 2006-036666 A | 2/2006 |
| JP | 3767627 | 2/2006 |
| JP | 2006-271351 | 10/2006 |
| KR | 2000-0072318 | 12/2000 |
| WO | 97-22629 | 6/1997 |
| WO | 02-04471 | 1/2002 |
| WO | WO 02/04471 | 1/2002 |
| WO | 02-074318 | 9/2002 |
| WO | 2004-084912 | 10/2004 |
| WO | WO 2004/084912 | 10/2004 |
| WO | 2006-101030 | 9/2006 |
| WO | WO 2006/101030 | 9/2006 |

OTHER PUBLICATIONS

Seikagaku. JP 2004-43645 A, Feb. 2004, machine translation.*
Armstrong et al. Biotechnology Techniques, vol. 9, No. 7, pp. 491-496, Jul. 1995.*
Murota et al. JP 2005110675, Apr. 28, 2005, abstract and machine translation.*
International Search Report, from PCT/JP2007/053183, mailed May 22, 2007.
European Search Report from EP07714683.5, mailed Feb. 8, 2011.
NHV Corporation, EPS Electron Beam Processing System (Brochure and Partial Translation), 4 pages (Sep. 2008).
Supplementary Search Report for EP 06 729 346.4 dated May 4, 2011 (3 pages).
1st Office Action for EP 06 729 346.4 dated Nov. 15, 2011 (2 pages).
Extended European Search Report for Application No. EP 12 00 1414.7 dated May 14, 2012 (5 pages).
English translation of 1st Office Action for Korean Application No. 10-2007-7024107 issued Oct. 25, 2010 (1 page).
English translation of 2nd Office Action for Korean Application No. 10-2007-7024107 issued Jan. 17, 2011 (4 pages).

(Continued)

*Primary Examiner* — Layla Bland
(74) *Attorney, Agent, or Firm* — Harness, Dickey & Pierce, P.L.C.

(57) ABSTRACT

A low-molecular-weight hyaluronic acid and/or its salt has an average molecular weight of 5000 to 20,000, and has a molecular weight distribution in which the proportion of components having a molecular weight of 10,000 or less is 40 wt % or more and the proportion of components having a molecular weight of 50,000 or more is 5 wt % or less.

12 Claims, 4 Drawing Sheets

OTHER PUBLICATIONS

English translation of Decision to Refuse a Patent for Korean Application No. 10-2007-7034107 issued Oct. 25, 2011 (1 page).
English translation of Decision to Maintain the Decision to Refuse a Patent for Korean Application No. 10-2007-7034107 issued May 19, 2011 (3 pages).
English translation of 1st Office Action for Chinese Application No. 2006-80008997.9 issued Nov. 27, 2009 (3 pages).
English translation of 2nd Office Action for Chinese Application No. 2006-80008997.9 issued Dec. 3, 2010 (2 pages).
English translation of 3rd Office Action for Chinese Application No. 2006-80008997.9 issued Feb. 24, 2011 (2 pages).
English translation of 1st Office Action for Chinese Application No. 2011-10008110.9 issued Feb. 2, 2012 (7 pages).
English translation of 1st Office Action for Japanese Application No. 2005-081571 dated Jun. 3, 2009 (5 pages).
English translation of 2nd Office Action for Japanese Application No. 2005-081571 dated Jan. 20, 2010 (6 pages).
English translation of 3rd Office Action for Japanese Application No. 2005-081571 dated May 18, 2010 (2 pages).
English translation of 1st Office Action for Japanese Application No. 2009-178669 dated May 22, 2012 (3 pages).
English translation of International Preliminary Report on Patentability for Application No. PCT/JP2006/305356 issued Aug. 12, 2008 (8 pages).
Supplementary European Search Report for Application No. 07 71 4683 mailed Jan. 19, 2011 (2 pages).
European Search Opinion for Application No. 07 71 4683 (2 pages).
English translation of 1st Office Action for European Application No. 07 714 683.5 mailed Oct. 27, 2011 (2 pages).
English translation of 1st Office Action for Chinese Application No. 2007-80006415.8 issued Dec. 1, 2010 (8 pages).
English translation of International Preliminary Report on Patentability for Application No. PCT/JP2007/053183 issued Aug. 26, 2008 (8 pages).
English translation of 1st Office Action for Japanese Application No. 2008-502722 dated Jun. 12, 2012 (5 pages).
T. Laurent et al., "Fractionation of Hyaluronic Acid, The Polydispersity of Hyaluronic Acid From the Bovine Vitreous Body", Biochemica et Biophysica Acta, 42, pp. 476-485, (1964).
Shoten, Horokawa, English translation of "The Japanese Pharmacopoeia", 14th Edition, (2006) (12 pages).
C. Yomota et al., "Evaluation of Molecular Weights of Hyaluronate Preparations by Multi-Angle Light Scattering", Bull. National Institute Health Sci., 121, 030-033 (2003) (5 pages).
English version of "The Japanese Pharmacopoeia, Fourteenth Edition", (2001) (6 pages).
R. Jeanloz et al., "The Degradation of Hyaluronic Acid by Methanolysis", vol. 3, No. 1, Nov. 26, 1962, pp. 121 and 122 (2 pages).
N. Jouon et al., "Hydration of Hyaluronic Acid As a Function of the Counterion Type and Relative Humidity", vol. 26, pp. 69-73 (1995) (5 pages).
C. Melander et al., "Carbohydrate Polymers", vol. 82, No. 3, pp. 874-879 (2010) (6 pages).
Y. Inoue et al., "Carbohydrate Research", vol. 141, No. 1, pp. 99-110 (1985) (12 pages).
N. Hartler et al., "Journal of Polymer Science", vol. 56, pp. 425-434 (1962) (10 pages).
L. Kudlacek et al. "The Effect of Heterogeneous Hydrolysis on the Structure of Cellulose", Polymer Science, USSR, vol. 6, No. 4, pp. 648-655 (1964) (8 pages).
Y. Brestkin et al., "Heterogeneous Degradation of Cellulose", Polymer Science, USSR, vol. 11, No. 11, pp. 2771-2778 (1969) (8 pages).
Pall Corporation, "Ultrafiltration Fundamentals," pp. 1-3 (2011) (3 pages).
"Protein Concentration and Sample Clarification" from Millipore [online], [retrieved Jan. 28, 2012 by U.S. PTO]. Retrieved from the internet <http://www.millipore.com/immunodetection/id3/concentration>.
"Hyaluronidase" Product Information Sheet from Sigma (2002) [online] [Retrieved Jul. 5, 2011 by U.S. PTO]. Retrieved from the internet <http://www.sigmaaldrich.com/etc/medialib/docs/Sigma/Product_Information_Sheet/2/h388 4pis.Par.0001.File.tmp/h3884pis.pdf>.

* cited by examiner

A   B   C

LOW MOLECULAR WEIGHT HYALURONIC ACID AND/OR SALT THEREOF, AND COSMETIC PREPARATION, PHARMACEUTICAL COMPOSITION, AND FOOD COMPOSITION EACH USING SAME

TECHNICAL FIELD

The present invention relates to a novel low-molecular-weight hyaluronic acid and/or its salt exhibiting excellent bioabsorbability, a cosmetic preparation, a pharmaceutical composition, and a food composition using the same.

BACKGROUND ART

Hyaluronic acid (average molecular weight: 500,000 to 2,000,000) is a mucopolysaccharide which exists in various tissues (e.g., subcutaneous tissues, eyeballs, and joints) of a living organism. Hyaluronic acid has been widely used as a cosmetic component due to high moisture retention properties (e.g., JP-A-2000-095660). It has been confirmed that oral administration of hyaluronic acid compensates for a decrease in hyaluronic acid content of a living body to improve the moisture retention, elasticity, and flexibility of the skin. Therefore, hyaluronic acid and its salts have been added to various types of food product.

However, since hyaluronic acid is a polysaccharide having a high molecular weight, hyaluronic acid is generally absorbed into a living body to only a small extent. For example, although evaporation of moisture through a skin can be prevented by applying hyaluronic acid, hyaluronic acid permeates the skin tissues to only a small extent and mainly remains on the surface of the skin due to its high molecular weight. Therefore, the skin moisturization effect may be lost if hyaluronic acid is washed away from the surface of the skin due to facial cleansing, bathing, or the like.

DISCLOSURE OF THE INVENTION

An object of the invention is to provide a novel low-molecular-weight hyaluronic acid and/or its salt exhibiting excellent bioabsorbability, a cosmetic preparation, a pharmaceutical composition, and a food composition using the same.

According to a first aspect of the invention, there is provided a low-molecular-weight hyaluronic acid and/or its salt having an average molecular weight of 5,000 to 20,000, the low-molecular-weight hyaluronic acid and/or its salt having a molecular weight distribution in which the proportion of components having a molecular weight of 10,000 or less is 40 wt % or more and the proportion of components having a molecular weight of 50,000 or more is 5 wt % or less.

The above low-molecular-weight hyaluronic acid and/or its salt may have a molecular weight distribution in which the proportion of components having a molecular weight of 10,000 or less is 40 wt % or more and the proportion of components having a molecular weight of 50,000 or more is 1 wt % or less. In this case, the proportion of components having a molecular weight of 10,000 or less may be 50 wt % or more.

The above low-molecular-weight hyaluronic acid and/or its salt may be produced by dispersing hyaluronic acid and/or its salt in an acidic aqueous medium.

The above low-molecular-weight hyaluronic acid and/or its salt may be produced by dispersing hyaluronic acid and/or its salt in an aqueous medium having a pH of 2 or less with heating, and drying by heating a residue obtained by removing the aqueous medium from the dispersion.

The above low-molecular-weight hyaluronic acid and/or its salt may have a kinematic viscosity of 2 $mm^2/s$ or less when prepared as a 1 wt % aqueous solution.

The absorbance ($A_{660}$) of a liquid obtained by adding a 0.5 g/mL cetylpyridinium chloride aqueous solution (0.05 g) to a 0.1 g/mL aqueous solution (10 mL) of the above low-molecular-weight hyaluronic acid and/or its salt may be 0.4 Abs or more.

The above low-molecular-weight hyaluronic acid and/or its salt may have a sodium chloride content of 0.5% or less.

According to a second aspect of the invention, there is provided a cosmetic preparation comprising the above low-molecular-weight hyaluronic acid and/or its salt.

According to a third aspect of the invention, there is provided a pharmaceutical composition comprising the above low-molecular-weight hyaluronic acid and/or its salt.

According to a fourth aspect of the invention, there is provided a food composition comprising the above low-molecular-weight hyaluronic acid and/or its salt.

The term "hyaluronic acid" used in the invention refers to a polysaccharide including at least one repeating unit formed of glucuronic acid and N-acetylglucosamine. The hyaluronic acid salt is not particularly limited. The hyaluronic acid salt is preferably a pharmaceutically acceptable salt. Examples of the hyaluronic acid salt include a sodium salt, a potassium salt, a calcium salt, a zinc salt, a magnesium salt, an ammonium salt, and the like of hyaluronic acid.

The above low-molecular-weight hyaluronic acid and/or its salt exhibits excellent bioabsorbability (e.g., percutaneous absorbability). Therefore, the low-molecular-weight hyaluronic acid and/or its salt may exhibit a skin improvement effect and the like. Accordingly, the above low-molecular-weight hyaluronic acid and/or its salt is useful as a component of a cosmetic preparation, a pharmaceutical composition, a food composition, and the like.

BEST MODE FOR CARRYING OUT THE INVENTION

Figure 1:
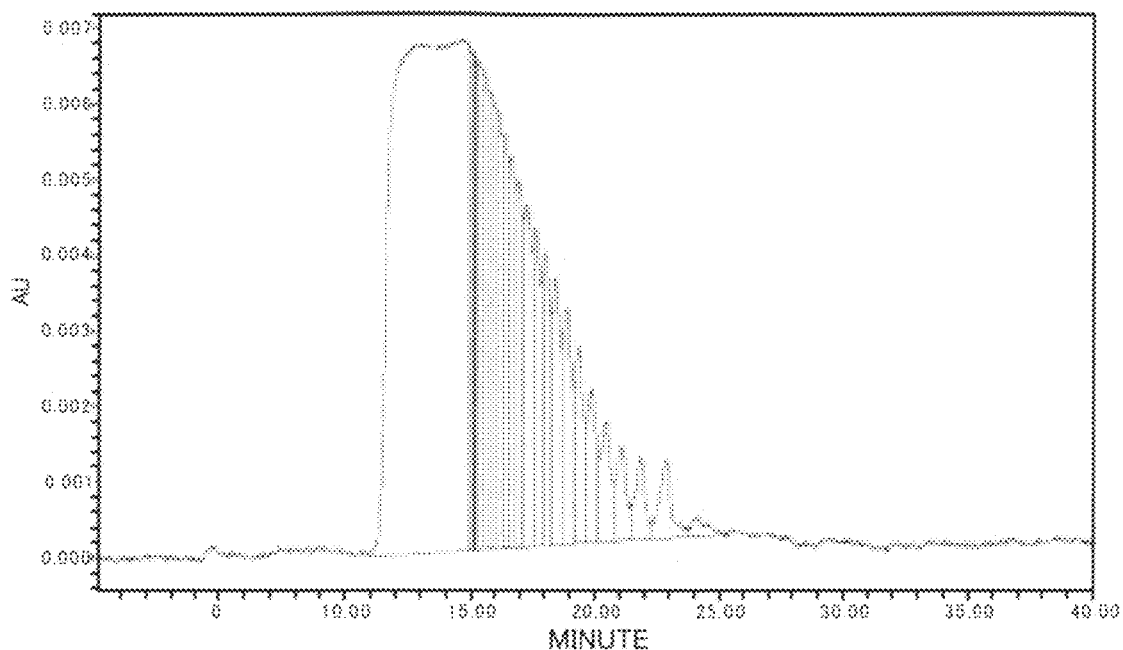
FIG. 1 shows a chromatogram of a low-molecular-weight hyaluronic acid obtained in Example 2.

A low-molecular-weight hyaluronic acid and/or its salt according to one embodiment of the invention, a cosmetic preparation, a pharmaceutical composition, and a food composition using the same are described in detail below. In the following embodiments and examples, "%" indicates "mass %".

1. Low-Molecular-Weight Hyaluronic Acid and/or its Salt

A low-molecular-weight hyaluronic acid and/or its salt according to one embodiment of the invention has an average molecular weight of 5,000 to 20,000, and has a molecular weight distribution in which the proportion of components having a molecular weight of 10,000 or less is 40 wt % or more and the proportion of components having a molecular weight of 50,000 or more is 5 wt % or less.

The low-molecular-weight hyaluronic acid and/or its salt exhibits excellent bioabsorbability. For example, the low-molecular-weight hyaluronic acid and/or its salt exhibits excellent percutaneous absorbability. When the low-molecular-weight hyaluronic acid and/or its salt is applied to a skin, the low-molecular-weight hyaluronic acid and/or its salt applied to the surface of the skin partially permeates the skin tissues. Specifically, since the moisture content of the skin can be maintained, the skin can be kept fresh.

The low-molecular-weight hyaluronic acid and/or its salt may be administered orally, or may be administered via percutaneous absorption, injection, or the like.

The average molecular weight of the low-molecular-weight hyaluronic acid and/or its salt is preferably 5,000 to 15,000, and more preferably 5,000 to 12,000 from the viewpoint of excellent bioabsorbability.

It is preferable for the low-molecular-weight hyaluronic acid and/or its salt that the proportion of components having a molecular weight of 10,000 or less be 40 wt % or more, and the proportion of components having a molecular weight of 50,000 or more be 1 wt % or less in view of bioabsorbability. It is more preferable that the proportion of components having a molecular weight of 10,000 or less be 50 wt % or more, and the proportion of components having a molecular weight of 50,000 or more be 1 wt % or less.

The average molecular weight and the molecular weight distribution defined in the invention are measured as follows.

1.1. Measurement of Average Molecular Weight

The average molecular weight defined in the invention refers to a molecular weight calculated from the limiting viscosity of a sample. In the invention, the average molecular weight of the low-molecular-weight hyaluronic acid and/or its salt is measured by calculating the limiting viscosity from the kinematic viscosity and converting the limiting viscosity into the molecular weight. Specifically, the kinematic viscosity is measured using an Ubbelohde viscometer described later, the limiting viscosity is calculated from the kinematic viscosity, and the limiting viscosity is converted into the average molecular weight.

In general, when calculating the limiting viscosity of a sample, a plurality of sample solutions are prepared. The specific viscosity and the reduced viscosity of the sample solution are calculated from the falling time (sec) of the sample solution and the falling time (sec) of the solvent determined using the Ubbelohde viscometer according to the following expressions (1) and (2).

$$\text{Specific viscosity} = \text{falling time (sec) of sample solution/falling time (sec) of solvent} - 1 \quad (1)$$

$$\text{Reduced viscosity} = \text{specific viscosity/sample concentration (dried product) (g/100 mL)} \quad (2)$$

A calibration curve for each sample solution is obtained by plotting the reduced viscosity along the vertical axis and the sample concentration (dried product) along the horizontal axis, and the limiting viscosity of the sample is determined by extrapolating the sample concentration to zero. When the sample is hyaluronic acid and/or its salt, the average molecular weight M of the sample can be calculated from the limiting viscosity of the sample according to the following expression (3).

$$\text{Limiting viscosity cm}^3/\text{g} = k' M^{alpha} \quad (3)$$

where, K' is 0.036, and alpha is 0.78.

The kinematic viscosity used as an index for calculating the molecular weight of the low-molecular-weight hyaluronic acid and/or its salt is measured as follows.

The kinematic viscosity of the low-molecular-weight hyaluronic acid and/or its salt may be measured using an Ubbelohde viscometer (manufactured by Sibata Scientific Technology Ltd.). In this case, an Ubbelohde viscometer having a coefficient such that the falling time is 200 to 1000 seconds is selected. The kinematic viscosity is measured in a thermostat bath at 30° C. while maintaining a constant temperature.

The kinematic viscosity (mm$^2$/s) can be calculated by multiplying the falling time (sec) of the aqueous solution measured using the Ubbelohde viscometer by the coefficient of the Ubbelohde viscometer.

The low-molecular-weight hyaluronic acid and/or its salt preferably has a kinematic viscosity (1 wt % aqueous solution) of 2 mm$^2$/s or less, more preferably 1.8 mm$^2$/s or less, and still more preferably 1.5 mm$^2$/s or less. If the low-molecular-weight hyaluronic acid and/or its salt has a kinematic viscosity (1 wt % aqueous solution) of more than 2 mm$^2$/s, preparation may become difficult due to too high a viscosity when the low-molecular-weight hyaluronic acid and/or its salt is added in an amount exceeding a specific amount, or the viscosity of the resulting cosmetic preparation, pharmaceutical composition, or food composition may be affected, whereby the feel may deteriorate, or the texture may be impaired.

1.2. Molecular Weight Distribution

The molecular weight distribution specifies the characteristics of the low-molecular-weight hyaluronic acid and/or its salt according to the invention.

The molecular weight distribution defined in the invention is determined by subjecting the sample of the low-molecular-weight hyaluronic acid and/or its salt to liquid chromatography analysis using a gel filtration column. The low-molecular-weight hyaluronic acid and/or its salt is a mixture of components that differ in molecular weight depending on the number of repeating units (N-acetyl-D-glucosamine and D-glucuronic acid). The components of the low-molecular-weight hyaluronic acid and/or its salt can be separated corresponding to the molecular size by subjecting the sample to liquid chromatography analysis using a gel filtration column.

When subjecting the low-molecular-weight hyaluronic acid and/or its salt to liquid chromatography analysis using a gel filtration column, the peaks of N-acetylglucosamine, D-glucuronic acid, hyaluronic acid (disaccharide: one repeating unit), hyaluronic acid (tetrasaccharide: two repeating units), hyaluronic acid (hexasaccharide: three repeating units), hyaluronic acid (octasaccharide: four repeating units), and the like are obtained along with the holding time. A holding time-molecular weight calibration curve of the hyaluronic acid is obtained based on the results, and the holding time corresponding to a given molecular weight is calculated from the calibration curve. The proportion of components within a given molecular weight range can be calculated by dividing the peaks corresponding to the holding time.

For example, the proportion of components having a molecular weight of 10,000 or less may be determined by calculating the holding time corresponding to the molecular weight of 10,000 from the calibration curve, and dividing the absorption area of components of which the holding time is equal to or shorter than the calculated holding time by the total absorption area. Likewise, the proportion of components having a molecular weight of 50,000 or more may be determined by calculating the holding time corresponding to the molecular weight of 50,000 from the calibration curve, and dividing the absorption area of components of which the holding time is equal to or longer than the calculated holding time by the total absorption area.

1.3. Measurement of Absorbance of Liquid Obtained by CPC Precipitation Method A CPC precipitation method is used for mucopolysaccharide confirmation tests. It is known that a mucopolysaccharide represented by hyaluronic acid can be bonded to a quaternary ammonium salt such as cetylpyridinium chloride (CPC) to precipitate.

In the invention, the absorbance of a liquid obtained by the CPC precipitation method may be used as an index for determining the presence or absence of the low-molecular-weight hyaluronic acid and/or its salt according to the invention.

It is preferable that a liquid obtained by adding a 0.5 g/mL cetylpyridinium chloride aqueous solution (CPC aqueous solution) (0.05 g) to a 0.1 g/mL aqueous solution (10 mL) of the low-molecular-weight hyaluronic acid and/or its salt according to this embodiment have an absorbance ($A_{660}$) of 0.4 Abs or more. The absorbance ($A_{660}$) refers to an absorbance of light having a wavelength of 660 nm, and is widely used as an index for identifying the turbidity of a liquid.

When preparing the above-mentioned mixed liquid the low-molecular-weight hyaluronic acid and/or its salt precipitates to only a small extent and the liquid tends to become cloudy, since the low-molecular-weight hyaluronic acid and/or its salt according to this embodiment has the above-mentioned molecular weight and molecular weight distribution. Specifically, the above-mentioned absorbance can be used as an index that indicated the presence or absence of the low-molecular-weight hyaluronic acid and/or its salt according to this embodiment.

1.4. Production

It is preferable to produce the low-molecular-weight hyaluronic acid and/or its salt by dispersing hyaluronic acid and/or its salt in an acidic aqueous medium. According to this method, since the resulting low-molecular-weight hyaluronic acid and/or its salt can be easily separated and purified as compared with a known method (e.g., the molecular weight of hyaluronic acid is reduced using an enzyme or the like or under alkaline conditions), the low-molecular-weight hyaluronic acid and/or its salt can be inexpensively produced with high yield.

1.4.1. Raw Material

Hyaluronic acid and its salt (hereinafter also referred to as "raw material hyaluronic acid and its salt") used as the raw material for the low-molecular-weight hyaluronic acid and/or its salt are generally obtained by extraction (and further purification, if necessary) from a biological tissue (e.g., cockscomb, umbilical cord, eyeball, skin, or cartilage), or a culture obtained by culturing a hyaluronic acid-producing microorganism (e.g., *Streptococcus* microorganism). For example, hyaluronic acid and/or its salt extracted from a cockscomb usually has a molecular weight of 2,000,000 to 8,000,000.

As the raw material hyaluronic acid and its salt, the above-mentioned unpurified extract or a purified product thereof may be used. It is preferable to use a purified product with a purity of hyaluronic acid and/or its salt of 90% (mass ratio) or more. When using a raw material hyaluronic acid and its salt with a purity of 90% or more, the raw material hyaluronic acid and its salt rarely cause a change in color tone or flavor during storage. As a result, a stable cosmetic preparation, pharmaceutical composition, and food composition can be obtained.

Note that the low-molecular-weight hyaluronic acid may be converted into the low-molecular-weight hyaluronic acid salt or the low-molecular-weight hyaluronic acid salt may be converted into the low-molecular-weight hyaluronic acid using a known method.

For example, the low-molecular-weight hyaluronic acid may be converted into the low-molecular-weight hyaluronic acid salt by treating the low-molecular-weight hyaluronic acid with an alkaline aqueous solution (e.g., an aqueous solution of sodium hydroxide, potassium hydroxide, calcium hydroxide, magnesium hydroxide, ammonium hydroxide, or the like). The low-molecular-weight hyaluronic acid salt may be converted into the low-molecular-weight hyaluronic acid by treating the low-molecular-weight hyaluronic acid salt with an acidic aqueous solution (e.g., an aqueous solution of hydrochloric acid, sulfuric acid, nitric acid, phosphoric acid, or the like), or may be converted into the low-molecular-weight hyaluronic acid using an acidic cation-exchange resin, for example.

1.4.2. Production Process

1.4.2-1. Dispersion Step

The low-molecular-weight hyaluronic acid and/or its salt may be produced by dispersing hyaluronic acid and/or its salt in an acidic aqueous medium, as described above.

In the dispersion step, a mixture obtained by adding powdery raw material hyaluronic acid and/or its salt to the acidic aqueous medium may be stirred, for example. The powdery hyaluronic acid and/or its salt is dispersed in the aqueous medium while being dissolved in the aqueous medium to only a small extent. Therefore, the powdery hyaluronic acid and/or its salt precipitates when stirring is stopped.

The degree of reduction in molecular weight may be adjusted by adjusting the stirring speed and the stirring time. The period of time in which the hyaluronic acid and/or its salt is dispersed in the acidic aqueous medium may be appropriately determined corresponding to the pH and the temperature of the acidic aqueous medium.

The low-molecular-weight hyaluronic acid and/or its salt which shows only a small degree of browning can be obtained by dispersing the raw material hyaluronic acid and/or its salt in the acidic aqueous medium. This makes purification for decolorization unnecessary, whereby a labor saving production process can be achieved.

The dispersion step may be carried out with heating. Specifically, a dispersion medium obtained by adding the powdery raw material hyaluronic acid and/or its salt to the acidic aqueous medium with stirring may be heated. Alternatively, the raw material hyaluronic acid and/or its salt may be added to the acidic aqueous medium heated in advance, and the temperature of the mixture may be maintained.

The heating temperature of the acidic aqueous medium is preferably 30 to 70° C. If the acidic aqueous medium is heated within this temperature range, the molecular weight of the raw material hyaluronic acid and/or its salt can be stably reduced to a desired value by heating within one hour. Note that the molecular weight of the raw material hyaluronic acid and/or its salt can also be reduced by performing the dispersion step at normal temperature (less than 30° C.) without heating the dispersion medium or the acidic aqueous medium. In this case, a very long time may be required as compared with the case of performing the dispersion step with heating. It is also possible to increase the heating temperature in the dispersion step to more than 70° C. In this case, the molecular weight of the raw material hyaluronic acid and/or its salt may reduced to a large extent when the raw material hyaluronic acid and/or its salt is heated for a long period of time. This may make it difficult to stably adjust the molecular weight to a desired value.

1.4.2-2. Drying by Heating Step

The process of producing the low-molecular-weight hyaluronic acid and/or its salt may include drying by heating a residue obtained by removing the acidic aqueous medium after dispersing the hyaluronic acid and/or its salt in the acidic aqueous medium.

In the drying by heating step, a residue obtained by removing the aqueous medium from the hyaluronic acid and/or its salt of which the molecular weight has been reduced by the dispersion step is dried by heating, for example. The aqueous medium may be removed by a physical means (e.g., filtration using a strainer or centrifugation) or evaporation using a rotary evaporator or the like, for example. In the drying by heating step, it is preferable to remove the remaining aqueous medium and water from the residue using a heating cabinet, a hot blast dryer, or the like.

The temperature for drying by heating and the time for drying by heating are not particularly limited. The temperature for drying by heating is preferably 60 to 95° C., more preferably 70 to 90° C., and still more preferably 70 to 80° C. If the temperature for drying by heating is less than 60° C., the drying efficiency may decrease. If the temperature for drying by heating exceeds 95° C., browning may occur. The time for drying by heating is preferably 6 to 48 hours, and more preferably 12 to 36 hours. If the time for drying by heating is less than six hours, the drying efficiency may decrease. If the time for drying by heating exceeds 48 hours, browning may occur.

Since the molecular weight of the hyaluronic acid and/or its salt of which the molecular weight has been reduced by the dispersion step can be further reduced by the drying by heating step, the molecular weight reduction efficiency can be improved. Moreover, the low-molecular-weight hyaluronic acid and/or its salt can be easily obtained by performing the drying by heating step.

1.4.2-3. Aqueous Medium

In the above-described production process, the term "aqueous medium" refers to a water-containing dispersion medium for hyaluronic acid and/or its salt. A medium which may be used for the aqueous medium preferably dissolves hyaluronic acid and/or its salt to only a small extent. A medium which may be used for the aqueous medium is not particularly limited. For example, it is preferable to use a liquid which is dissolved in water and can be used in the production of cosmetics or food products. Examples of the medium which may be used for the aqueous medium include alcohol media (e.g., methanol, ethanol, n-propanol, and 2-propanol), ketone media (e.g., acetone and methyl ethyl ketone), tetrahydrofuran, acetonitrile, and the like. These media may be used either individually or in combination. The medium used for the aqueous medium is preferably at least one medium selected from ethanol, methanol, and acetone due to a low boiling point and low cost.

The water content of the aqueous medium is not particularly limited. If the water content of the aqueous medium is too high, hyaluronic acid and/or its salt may not be maintained in a dispersed state but be dissolved in the aqueous medium, whereby the yield may decrease. Accordingly, the water content of the aqueous medium is preferably 40 vol % or less, and more preferably 30 vol % or less based on the total amount of the aqueous medium.

In the above-described production process, an acid or an acidic cation-exchange resin may be used to acidify the aqueous medium, for example.

The acid used to acidify the aqueous medium is not particularly limited. An acid which can be used in the production of cosmetics, medicines, or food products is preferably used. Examples of the acid include inorganic acids such as hydrochloric acid, sulfuric acid, nitric acid, and phosphoric acid, and organic acids such as citric acid, ascorbic acid, acetic acid, and glacial acetic acid. The amount of acid to be added is not particularly limited. If the amount of acid is too small, since the molecular weight of hyaluronic acid and/or its salt may not be reduced sufficiently, the production efficiency may decrease. If the amount of acid is too large, since a reduction in the molecular weight of hyaluronic acid and/or its salt may be promoted, it may be difficult to stably adjust the molecular weight to a desired value. For example, when using hydrochloric acid as the acid, hydrochloric acid is preferably used in an amount of 0.2 to 4 vol %. When using sulfuric acid as the acid, sulfuric acid is preferably used in an amount of 0.1 to 3 vol %.

The acidic cation-exchange resin is not particularly limited. Examples of the acidic cation-exchange resin include a strongly acidic cation-exchange resin, a weakly acidic cation-exchange resin, and the like. It is preferable to use a strongly acidic cation-exchange resin as the acidic cation-exchange resin.

In the above-described production process, the pH of the aqueous medium is preferably 2 or less, and more preferably 1 or less. If the pH of the aqueous medium is more than 2, it may take time to reduce the molecular weight of the raw material hyaluronic acid and/or its salt, whereby efficiency may decrease.

1.5. Difference in Production Process and Difference in Sodium Chloride Content In the invention, the sodium chloride content of hyaluronic acid may be used as an index for determining the presence or absence of the low-molecular-weight hyaluronic acid and/or its salt according to the invention.

The low-molecular-weight hyaluronic acid and/or its salt according to this embodiment preferably has a sodium chloride content of 0.5% or less. The sodium chloride content of the low-molecular-weight hyaluronic acid and/or its salt according to this embodiment is more preferably 0.3% or less.

Hyaluronic acid generally contains sodium chloride in an amount that differs depending on the industrial production process. The sodium chloride content is normally 1% or more. Example of the hyaluronic acid industrial production process include a purification method by means of ethanol precipitation and a purification method using a quarternary ammonium salt (FRAGRANCE JOURNAL, special issue, No. 15 1996 (separate print)).

The purification method by means of ethanol precipitation is normally carried out as follows. Sodium chloride is added to a hyaluronic acid extract, and ethanol is added to the mixture in an amount twice to three times the amount of the extract. Hyaluronic acid precipitates due to the addition of ethanol. Impurities are separated from hyaluronic acid in a dissolved state. This step is repeated to increase the purity of hyaluronic acid. The resulting product is washed with aqueous ethanol several times to remove sodium chloride.

The purification method using a quarternary ammonium salt is carried out as follows. Hyaluronic acid forms a composite with a quarternary ammonium salt and precipitates. Therefore, a quarternary ammonium salt is added to a hyaluronic acid extract to effect precipitation. The resulting precipitate is washed with a sodium chloride-containing alcohol. The washing step is repeated several times to increase the purity of hyaluronic acid. The resulting product is washed with aqueous ethanol several times to remove sodium chloride.

In either method, since a large amount of sodium chloride is used during purification, a certain amount of sodium chloride remains in spite of the sodium chloride removal step.

In the production process according to this embodiment, a hyaluronic acid powder is heated in a hydrochloric acid-containing aqueous ethanol in a powdery state, followed by several washing operations with aqueous ethanol to remove hydrochloric acid (the details are described later). Since the production process according to this embodiment does not require powder formation, sodium chloride need not be added. Moreover, since hydrochloric acid is removed by washing and drying without neutralization, the content of sodium chloride/chlorine ions is reduced to a very low level. Therefore, the resulting hyaluronic acid and/or its salt has a sodium chloride content of 0.5% or less (preferably 0.3% or less).

The production process according to this embodiment can reduce the sodium chloride content to about 0.05% (see examples described later). Note that the sodium chloride content may be further reduced by desalting, an ion-exchange process, or the like. The sodium chloride content of the hyaluronic acid and/or its salt according to this embodiment can thus be reduced to 1/100th or less of the sodium chloride content of normal hyaluronic acid.

The low-molecular-weight hyaluronic acid and/or its salt according to this embodiment is used for a cosmetic preparation, a pharmaceutical composition, or a food composition (see test examples described later). In this case, salts such as sodium chloride may impair the stability of the system. In particular, an emulsified system may be demulsified. Since a cosmetic preparation, a pharmaceutical composition, or a food composition is directly applied to a skin or hair or is eaten, it is desirable that the amount of remaining salts such as sodium chloride be reduced as much as possible.

2. Cosmetic Preparation

A cosmetic preparation according to one embodiment of the invention comprises the low-molecular-weight hyaluronic acid and/or its salt. The form of the cosmetic preparation is not particularly limited. Examples of the form of the cosmetic preparation include a skin cleansing preparation, toilet lotion (e.g., whitening lotion), cream (e.g., vanishing cream and cold cream), milky lotion, essence, pack, foundation, rouge, lip balm, lip gloss, lip liner, cheek rouge, nail treatment agent, mascara, eyeliner, eyebrow powder, cleansing, facial wash, shampoo, rinse, hair treatment agent, hair conditioner, hair styling agent, hair mask, hair tonic, pilatory, shaving lotion, after-shave lotion, after-sun lotion, deodorant lotion, body lotion (including hand care lotion and foot care lotion), body oil, perm solution, coloring solution, soap, body soap, bath agent, and the like.

Since the low-molecular-weight hyaluronic acid and/or its salt contained in the cosmetic preparation according to this embodiment permeates skin tissues and exhibits water retention properties, the cosmetic preparation according to this embodiment can maintain the skin moisture content and keep the skin fresh.

3. Pharmaceutical Composition

A pharmaceutical composition according to one embodiment of the invention comprises the low-molecular-weight hyaluronic acid and/or its salt. The pharmaceutical composition may be an external preparation or an internal preparation, for example. Examples of the external preparation include ointment, an external liquid preparation (e.g., ophthalmic solution and gargle), nose drops, eardrops, an adhesive preparation (e.g., poultice and plaster agent), a suppository, lotion, liniment, aerosol, and the like. Examples of the internal preparation include a troche, an internal liquid preparation, a chewable preparation, and the like.

Since the pharmaceutical composition according to this embodiment contains the low-molecular-weight hyaluronic acid and/or its salt, the pharmaceutical composition exhibits excellent bioabsorbability. For example, when the pharmaceutical composition is an external preparation, since the low-molecular-weight hyaluronic acid and/or its salt contained in the external preparation permeates skin tissues and exhibits water retention properties, the external preparation can maintain the skin moisture content and keep the skin fresh. For example, when the pharmaceutical composition is an internal preparation, since the low-molecular-weight hyaluronic acid and/or its salt contained in the internal preparation permeates oral tissues and exhibits water retention properties, the internal preparation exhibits a mouth moisturization effect.

4. Food Composition

A food composition according to one embodiment of the invention comprises the low-molecular-weight hyaluronic acid and/or its salt. The form of the food composition is not particularly limited. Examples of the form of the food composition include food compositions which may exhibit a mouth moisturization effect such as gum, candy, gummy candy, food products in the form of troche, and jelly beverages, general food products including staple foods such as rice products and bread, dishes other than staple foods such as retort (canned) foods, frozen foods, daily dishes, and dry foods, seasonings such as mayonnaise, beverages, confectioneries, desserts, and liquid, gelled, or soft-capsuled supplements, and general foods for specified health use for which use of health claims is allowed.

Since the low-molecular-weight hyaluronic acid and/or its salt contained in the food composition according to this embodiment permeates oral tissues and exhibits water retention properties, the food composition exhibits a mouth moisturization effect.

5. Examples

The invention is described below in more detail by way of examples, comparative examples, and test examples. Note that the invention is not limited to the following examples. Measurement of kinematic viscosity and calculation of limiting viscosity were conducted using the above-described methods.

5.1. Evaluation Method

Low-molecular-weight hyaluronic acids obtained in Examples 1 to 3 described later were subjected to measurements of the molecular weight distribution and the absorbance of a liquid obtained by the CPC precipitation method as follows.

5.1.1. Molecular Weight Distribution

A gel filtration column ("Diol-120" manufactured by YMC Co., Ltd.) was connected to an HPLC analysis system ("Alliance PDA system" manufactured by Nihon Waters K.K.). A 0.1% (w/v) aqueous solution of the low-molecular-weight hyaluronic acid was prepared as an analysis sample. The molecular weight distribution of the low-molecular-weight hyaluronic acid was measured by subjecting the analysis sample to liquid chromatography analysis. FIG. 1 shows a chromatogram of the low-molecular-weight hyaluronic acid obtained in Example 2.

The liquid chromatography analysis conditions were as follows.
Column temperature: 40° C.
Flow rate: 1 mL/min
Injection amount of 0.1% (w/v) aqueous solution of low-molecular-weight hyaluronic acid: 20 microliters
Mobile phase: 0.003M phosphoric acid buffer (containing 0.15M NaCl, pH: 7.0)

According to liquid chromatography using the gel filtration column employed in the examples, the molecular weight decreases as the holding time increases. As shown in FIG. 1, the peaks of N-acetylglucosamine, D-glucuronic acid, hyaluronic acid (disaccharide: one repeating unit), hyaluronic acid (tetrasaccharide: two repeating units), hyaluronic acid (hexasaccharide: three repeating units), hyaluronic acid (octasaccharide: four repeating units), and the like were obtained from the right along with the holding time. The holding time and the molecular weight at each peak were calculated, and a holding time-molecular weight calibration curve was determined (expression 5).

In the expression 5, x indicates the holding time, and y indicates the molecular weight. The holding time corresponding to a given molecular weight (10,000 or 50,000) is calculated from the calibration curve shown by the expression 5. The proportion of components within a given molecular weight range was calculated by dividing the peaks corresponding to the holding time. The molecular weight corresponding to each peak was identified by utilizing a peak observed in a chromatogram obtained by similarly subjecting the minimum constituent unit (disaccharide) of hyaluronic acid having a known molecular weight to liquid chromatography analysis.

For example, the proportion of components having a molecular weight of 10,000 or less was determined by calculating the holding time corresponding to the molecular weight of 10,000 from the calibration curve shown by the expression 5, and dividing the absorption area of components corresponding to the holding time equal to or shorter than the calculated holding time by the total absorption area. Likewise, the proportion of components having a molecular weight of 50,000 or more was determined by calculating the holding time corresponding to the molecular weight of 50,000 from the calibration curve shown by the expression 5, and dividing the absorption area of components corresponding to the holding time equal to or longer than the calculated holding time by the total absorption area.

Table 1 shows the relationship between the number of repeating units of each molecular weight component and the holding time obtained from the chromatogram shown in FIG. 1 as an example.

TABLE 1

| Number of repeating units | Holding time (min) | Molecular weight (Da) |
|---|---|---|
| 1 | 21.867 | 379 |
| 2 | 21.099 | 758 |
| 3 | 20.454 | 1137 |
| 4 | 19.870 | 1516 |
| 5 | 19.360 | 1895 |
| 6 | 18.874 | 2274 |
| 7 | 18.441 | 2653 |
| 8 | 18.034 | 3032 |
| 9 | 17.635 | 3411 |
| 10 | 17.289 | 3790 |
| 11 | 16.951 | 4169 |
| 12 | 16.648 | 4548 |
| 13 | 16.332 | 4927 |
| 14 | 16.102 | 5306 |
| 15 | 15.860 | 5685 |
| 16 | 15.622 | 6064 |
| 17 | 15.400 | 6443 |
| 18 | 15.232 | 6822 |
| 19 | 15.148 | 7201 |
| 20 | 15.047 | 7580 |
| 21 | 14.898 | 7959 |
| 22 | 14.715 | 8338 |

*The molecular weight of the hyaluronic acid was calculated as a free acid.

$$y=-21.4x^3+1296.2x^2-26747.1x+189427.1 \tag{5}$$

5.1.2. Measurement of Absorbance of Liquid Obtained by CPC Precipitation Method In the examples, the absorbance of a liquid obtained by the CPC precipitation method was measured as follows.

0.01 g of the low-molecular-weight hyaluronic acid according to the invention was dissolved in 10 mL of distilled water to prepare a 0.1 (g/mL) hyaluronic acid aqueous solution. 1 g of CPC was dissolved in 20 mL of distilled water to prepare a 0.05 (g/mL) CPC aqueous solution. 52 microliters (0.05 g) of the 0.05 (g/mL) CPC aqueous solution was added to 10 mL of the 0.1 (g/mL) hyaluronic acid aqueous solution. After sufficiently stirring the mixture, the absorbance at 660 nm (turbidity) was measured after five minutes.

Figure 2:
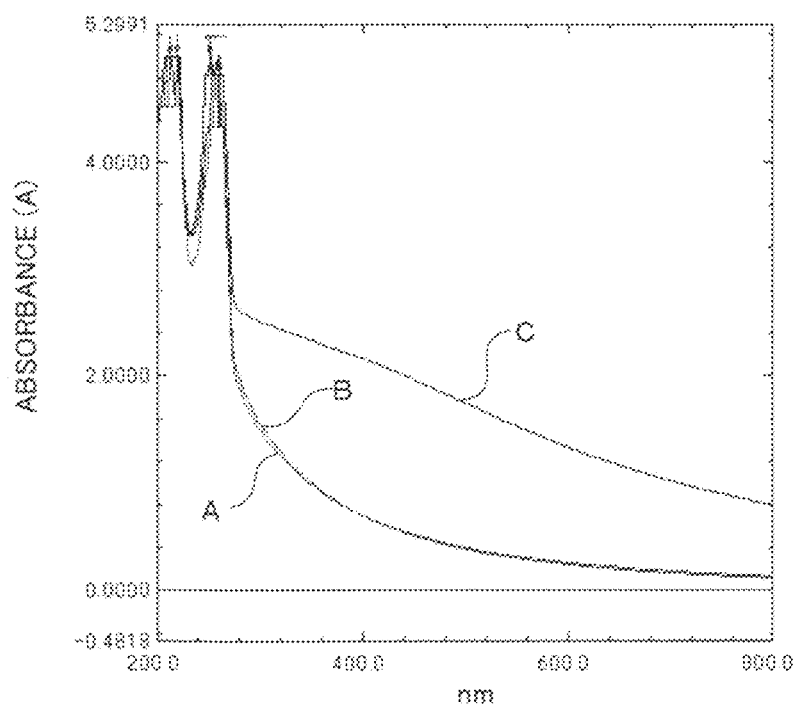
FIG. 2 shows the measurement results for the absorbance of a liquid obtained by adding a CPC solution to a liquid containing a low-molecular-weight hyaluronic acid (sample C) obtained in Example 2.

FIG. 2 shows the measurement results for the absorbance of the low-molecular-weight hyaluronic acid (sample C) obtained in Example 2 determined using the above-described method. A similar test was conducted on hyaluronic acids (samples A and B) having known molecular weights as controls.

Figure 3:
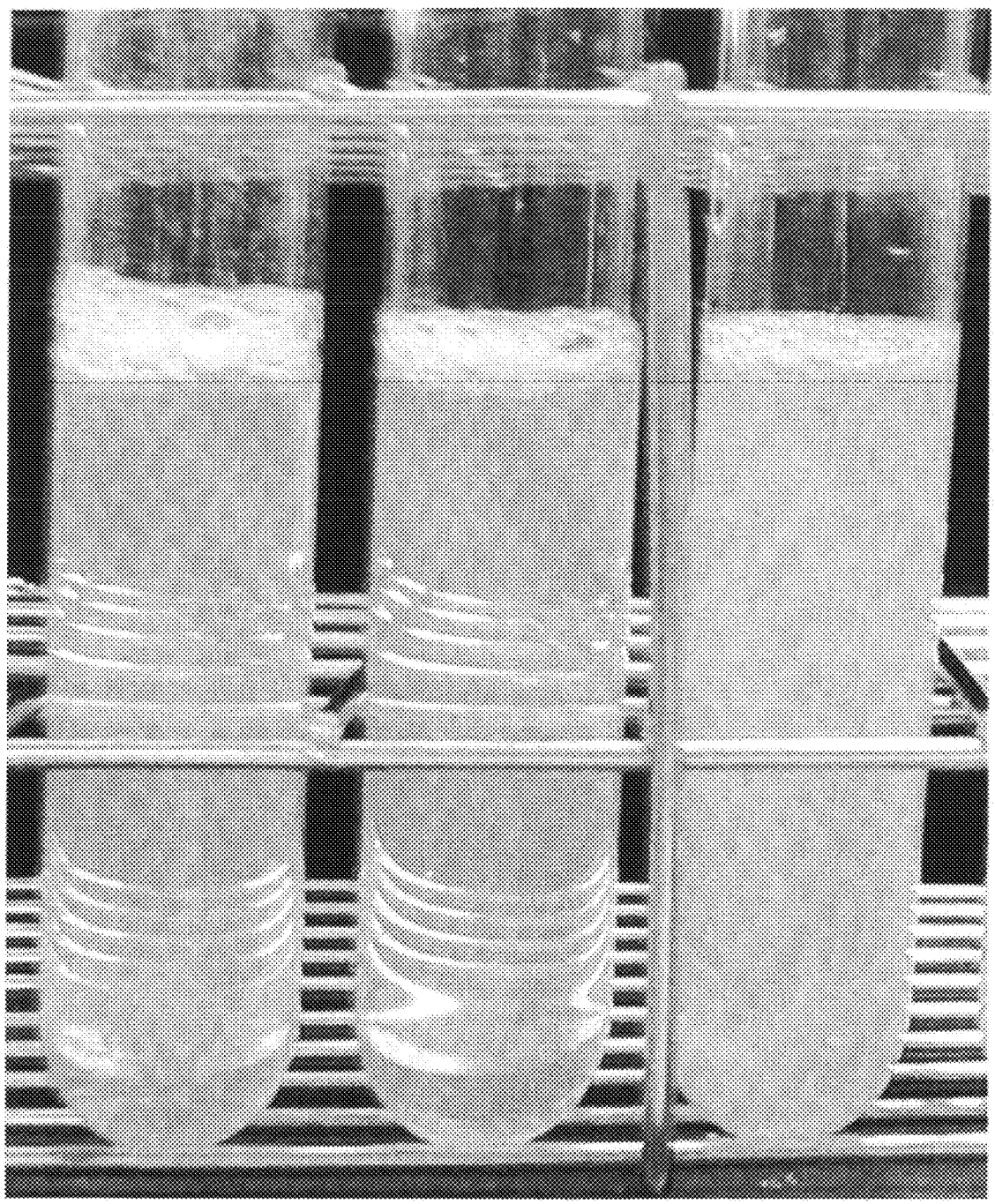
FIG. 3 shows photographs of liquids obtained by adding a CPC solution to liquids respectively containing samples A to C.

The sample A is Hyaluronsan HA-L510 (manufactured by Q.P. Corporation), and the sample B is Hyaluronic Acid FCH FCH-A (manufactured by Kibun Food Chemifa Co., Ltd.). FIG. 3 shows the photographs of the samples A to C subjected to the absorbance measurement.

TABLE 2

| Sample | Molecular weight | Absorbance |
|--------|------------------|------------|
| A | 80,000 | 0.16 |
| B | 30,000 | 0.22 |
| C | 6,000 | 0.58 |

As shown in FIG. 2 (absorbance measurement results for light having different wavelengths), the samples A and B showed behavior significantly differing from that of the sample C. As shown in FIG. 3, a significant difference in turbidity was observed with the naked eye between the samples A and B and the sample C. Specifically, when using the sample C (i.e., an aqueous solution of the low-molecular-weight hyaluronic acid obtained in Example 2), the liquid did not undergo precipitation even if the CPC aqueous solution was added, but merely became cloudy due to its molecular weight and molecular weight distribution. On the other hand, when performing the above-described operation using the sample A or B, precipitation occurred when the CPC aqueous solution was added. Therefore, the transparency of the liquid was higher than that of the liquid using the sample C.

These results suggest that the absorbance of the liquid obtained by the CPC precipitation method is an index that indicates the difference in characteristics between the low-molecular-weight hyaluronic acid according to the invention and hyaluronic acid having a higher molecular weight.

The low-molecular-weight hyaluronic acids obtained in Examples 1 and 3 described later were also subjected to the measurement of the absorbance of a liquid obtained by the CPC precipitation method. The results are described in each example.

5.1.3. Measurement of Sodium Chloride Content

In the examples, the sodium chloride content of the low-molecular-weight hyaluronic acid was measured as follows using the Mohr method.
(Measurement Method)
2.5 g of the low-molecular-weight hyaluronic acid obtained in Example 1 was dissolved in 100 mL of distilled water. 1 mL of a 10% potassium chromate solution was added to the low-molecular-weight hyaluronic acid aqueous solution. After sufficiently stirring the mixture, the mixture was titrated with a silver nitrate solution until the mixture became slightly brown. The sodium chloride content of the low-molecular-weight hyaluronic acid was calculated using the following expression (4).

$$\text{Sodium chloride content (\%)} = (X \times \text{titer (mL)}) / (\text{amount of sample (g)} \times 1000) \times 100 \quad (4)$$

where, X indicates the factor of the silver nitrate solution (X=13.345 in this test).
(Measurement Results)
Table 3 shows the measurement result for the sodium chloride content of the low-molecular-weight hyaluronic acid (sample A) obtained in Example 1 determined using the above-described method. A similar test was conducted using hyaluronic acids (samples B and C) produced using a known method (e.g., ethanol precipitation) as controls to determine the sodium chloride content. The sample C is Hyaluronsan HA-LF (manufactured by Q.P. Corporation, average molecular weight: 300,000), and the sample B is Hyaluronic Acid FCH FCH-A (manufactured by Kibun Food Chemifa Co., Ltd., average molecular weight: 30,000).

TABLE 3

| Sample | Sodium chloride content |
|--------|------------------------|
| A | 0.19% |
| B | 1.26% |
| C | 1.15% |

As shown in Table 3, a significant difference in sodium chloride content was observed between the sample A and the samples B and C.

Specifically, the sodium chloride content is an index that indicates the difference in characteristics between the low-molecular-weight hyaluronic acid according to the invention and hyaluronic acid produced by a known method.

The sodium chloride content of the low-molecular-weight hyaluronic acids obtained in Examples 2 and 3 described later was also measured using the above-described method. The results are described in each example.

5.2. Example 1

In this example, a sodium hyaluronate (hereinafter also referred to as "HANa") fine powder extracted from a cockscomb and then purified was provided as a raw material. The average molecular weight and the purity of the raw material HANa were respectively about 2,100,000 and 97%.

A tank (volume: 300 liters) equipped with a stirrer and a jacket was charged with 110 liters of 80% aqueous acetone (acidic aqueous medium) containing 0.5% of sulfuric acid. The aqueous acetone was heated to 60° C. with stirring. The pH of the treatment liquid was 1.08. Note that 80% aqueous acetone contains 80% (W/W) of acetone and 20% (W/W) of water, and 80% aqueous acetone containing 0.5% of sulfuric acid contains 0.5% (W/W) of sulfuric acid and 99.5% (W/W) of 80% aqueous acetone. After the temperature reached 60° C., 6 kg of the raw material HANa fine powder was added to the tank with stirring. The mixture was stirred so that the raw material HANa fine powder was dispersed while heating the mixture so that the temperature of the sulfuric acid-containing aqueous acetone was maintained at 60° C.

After 15 minutes, the mixture was allowed to stand. The supernatant sulfuric acid-containing aqueous acetone was then removed by decantation to obtain a precipitate. After the addition of 110 liters of 80% aqueous acetone containing 0.5% of sulfuric acid (heated to 60° C. in advance) to the resulting precipitate, the mixture was stirred for 15 minutes while heating the mixture at 60° C. This operation was carried out three times in total.

After the addition of 110 liters of 80% aqueous acetone to the precipitate obtained after removing the sulfuric acid-containing aqueous acetone, the mixture was stirred for 15 minutes in order to remove residual sulfuric acid. This operation was repeated until the sulfuric acid was completely removed.

The aqueous acetone was then removed by decantation to obtain a residue. After further removing the aqueous acetone by subjecting the residue to centrifugation, the resulting product was dried at 70° C. for 12 hours under reduced pressure using a vacuum dryer.

5.3 kg (yield: about 88%) of low-molecular-weight hyaluronic acid was thus obtained as a fine white powder. The kinematic viscosity of a 1% aqueous solution of the low-molecular-weight hyaluronic acid measured using an Ubbelohde viscometer was 1.5 mm$^2$/s. The average molecular weight of the low-molecular-weight hyaluronic acid converted from the limiting viscosity was 9,000. The low-molecular-weight hyaluronic acid had a molecular weight distribution in which the proportion of components having a molecular weight of 10,000 or less was 49 wt % or more and the proportion of components having a molecular weight of 50,000 or more was 0.5 wt %. The absorbance ($A_{660}$) of a liquid obtained by adding a 0.5 g/mL cetylpyridinium chloride aqueous solution (0.05 g) to a 0.1 g/mL aqueous solution (10 mL) of the low-molecular-weight hyaluronic acid was 0.57 Abs.

5.3. Example 2

In this example, the HANa fine powder used in Example 1 was provided as a raw material.

A tank (volume: 300 liters) equipped with a stirrer and a jacket was charged with 110 liters of 73% aqueous ethanol (acidic aqueous medium) containing 2% of hydrochloric acid. The aqueous ethanol was heated to 50° C. with stirring. The pH of the treatment liquid was 0.70. Note that 73% aqueous ethanol contains 73% (W/W) of ethanol and 27% (W/W) of water, and 73% aqueous ethanol containing 2% of hydrochloric acid contains 2% (W/W) of hydrochloric acid and 98% (W/W) of 73% aqueous ethanol. After the temperature reached 50° C., 6 kg of the raw material HANa fine powder was added to the tank with stirring. The mixture was stirred so that the raw material HANa fine powder was dispersed while heating the mixture so that the temperature of the hydrochloric acid-containing aqueous ethanol was maintained at 60° C.

After 15 minutes, the mixture was allowed to stand. The supernatant hydrochloric acid-containing aqueous ethanol was then removed by decantation to obtain a precipitate. After the addition of 110 liters of 73% aqueous ethanol containing 2% of hydrochloric acid (heated to 50° C. in advance) to the resulting precipitate, the mixture was stirred for 15 minutes while heating the mixture at 50° C. This operation was carried out three times in total.

After the addition of 110 liters of 73% aqueous ethanol to the precipitate obtained following removal of the hydrochloric acid-containing aqueous ethanol, the mixture was stirred for 15 minutes in order to remove residual hydrochloric acid. This operation was repeated until the hydrochloric acid was completely removed.

The aqueous ethanol was then removed by decantation to obtain a residue. After further removing the aqueous ethanol by subjecting the residue to centrifugation, the resulting product was dried at 80° C. for 24 hours under reduced pressure using a vacuum dryer.

5.5 kg (yield: about 92%) of low-molecular-weight hyaluronic acid was thus obtained as a fine white powder. The kinematic viscosity of a 1% aqueous solution of the low-molecular-weight hyaluronic acid measured using an Ubbelohde viscometer was 1.1 mm$^2$/s. The average molecular weight of the low-molecular-weight hyaluronic acid converted from the limiting viscosity was 6,000. The low-molecular-weight hyaluronic acid had a molecular weight distribution in which the proportion of components having a molecular weight of 10,000 or less was 58 wt % or more and the proportion of components having a molecular weight of 50,000 or more was 0.2 wt %. The absorbance ($A_{660}$) of a liquid obtained by adding a 0.5 g/mL cetylpyridinium chloride aqueous solution (0.05 g) to a 0.1 g/mL aqueous solution (10 mL) of the low-molecular-weight hyaluronic acid was 1.16 Abs. The sodium chloride content of the low-molecular-weight hyaluronic acid was 0.10%.

5.4. Example 3

In this example, a raw material hyaluronic acid (hereinafter also referred to as "HA") fine powder was provided which was extracted from a hyaluronic acid-containing fermented product obtained by culturing hyaluronic acid-producing *Streptococcus* microorganisms and then purified. The average molecular weight and the purity of the raw material HA were respectively about 1,600,000 and 97%.

A tank (volume: 300 liters) equipped with a stirrer was charged with 110 liters of 80% aqueous ethanol (acidic aqueous medium) containing 2% of hydrochloric acid. The aqueous ethanol was heated to 70° C. with stirring. The pH of the treatment liquid was 0.76. Note that 80% aqueous ethanol contains 80% (W/W) of ethanol and 20% (W/W) of water, and 80% aqueous ethanol containing 2% of hydrochloric acid contains 2% (W/W) of hydrochloric acid and 98% (W/W) of 80% aqueous ethanol. After the temperature reached 70° C., 6 kg of the raw material HA fine powder was added to the tank with stirring. The mixture was stirred so that the raw material HA powder was dispersed while controlling the temperature so that the temperature of the hydrochloric acid-containing aqueous ethanol was maintained at 70° C.

After 60 minutes, the mixture was allowed to stand. The supernatant hydrochloric acid-containing aqueous ethanol was then removed by decantation to obtain a residue. After further removing the aqueous ethanol by subjecting the residue to centrifugation, the resulting product was dried at normal temperature for 12 hours under reduced pressure using a vacuum dryer in the presence of silica gel. 5.5 kg (yield: about 92%) of low-molecular-weight hyaluronic acid was thus obtained as a fine white powder. The kinematic viscosity of a 1% aqueous solution of the low-molecular-weight hyaluronic acid measured using an Ubbelohde viscometer was 1.8 mm$^2$/s. The average molecular weight of the low-molecular-weight hyaluronic acid converted from the limiting viscosity was 14,000. The low-molecular-weight hyaluronic acid had a molecular weight distribution in which the proportion of components having a molecular weight of 10,000 or less was 43 wt % or more and the proportion of components having a molecular weight of 50,000 or more was 2.1 wt %. The absorbance ($A_{660}$) of a liquid obtained by adding a 0.5 g/mL cetylpyridinium chloride aqueous solution (0.05 g) to a 0.1 g/mL aqueous solution (10 mL) of the low-molecular-weight hyaluronic acid was 0.44 Abs. The sodium chloride content of the low-molecular-weight hyaluronic acid was 0.07%.

5.5. Test Example 1

In this test example, the low-molecular-weight hyaluronic acid according to the invention was percutaneously administered to a mouse to evaluate the percutaneous absorbability of the low-molecular-weight hyaluronic acid.

5.5.1. Test Method

5.5.1-1. Experimental Animals

Six-week-old (when the test was started) male hairless mice (Hos: HR-1) (purchased from Japan SLC Inc.)
The mice were acclimatized for one week before the test.

5.5.1-2. Sample

Sample 1: low-molecular-weight hyaluronic acid obtained in Example 2
Sample 2: hyaluronic acid ("Hyaluronsan HA-LQH" manufactured by Q.P. Corporation, molecular weight: 1,800,000)
Sample 3 (control): distilled water

5.5.1-3. Preparation of Fluorescent Sample

In order to distinguish the applied sample from hyaluronic acid present in the skin, the hyaluronic acids used as the samples 1 and 2 were labeled with a fluorescent substance (DMEQ-hydrazide) before the test. Specifically, the hyaluronic acid was labeled with a fluorescent substance by allowing a carboxylic acid group of the hyaluronic acid to react with DMEQ-hydrazide. The hyaluronic acid fluorescent labeling method used is disclosed in "Effects of ultrasonic application on skin absorption of sodium hyaluronate (ceratin moisturizing agent)" (Meihua Li, Hideo Ueda, et al., Drug Delivery System, 12, pp. 415 to 419 (1997)), for example.

5.5.1-4. Sample Group

Test group 1: fifteen mice to which a 1% aqueous solution of the fluorescent sample 1 was attached
Test group 2: fifteen mice to which a 1% aqueous solution of the fluorescent sample 2 was attached
Sample 3 (control): fifteen mice to which distilled water was applied

5.5.1-5. Test Method

Cotton lint (1 cm$^2$) provided with 100 mg of the fluorescent sample or distilled water was attached to the abdomen of each mouse. The cotton lint was removed from five mice in each test group after 1, 3, and 5 hours. The sample that remained on the surface of the skin was washed with water. After sufficiently drying the skin, about 1 cm$^2$ of the skin to which the sample was applied was loosened with scissors and removed. The peritoneum appeared after collecting the skin of the mouse (i.e., the corium was also collected).

A centrifuge tube was charged with the removed skin. After the addition of 2 mL of distilled water, the mixture was homogenized and then centrifuged (3000 rpm) at 4° C. for 10 minuites. The supernatant liquid was collected and used as an analysis sample. The amount of the fluorescent substance in the analysis sample was measured to evaluate whether or not the sample 1 or 2 had permeated the skin.

A Student's t-test was conducted on the test group 3 (control group) and the test group 1, and on the test group 3 and the test group 2 to determine the presence or absence of a significant difference (P<0.05).

5.5.1-6. HPLC Analysis Conditions and Analysis Results

Figure 4:
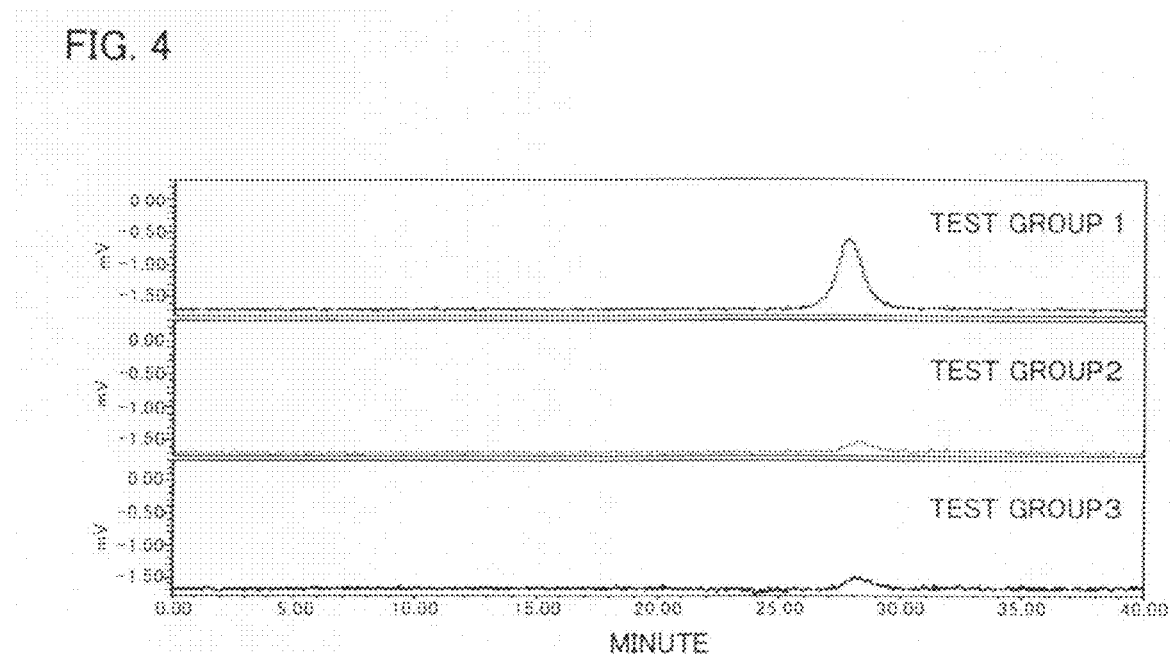
FIG. 4 shows an HPLC analysis chart of analysis samples of test groups 1 to 3 to which a sample was attached for five hours in Test Example 1.

The analysis sample (supernatant liquid) obtained by the above-described test method was subjected to HPLC analysis. The HPLC analysis conditions were as follows.
Analyzer: Waters 2690 470
Column: Shodex suger KS807 (gel filtration column)
Column temperature: 40° C.
Flow rate: 0.5 mL/min
Injection amount: 20 microliters
Mobile phase: 0.003 mol/L phosphoric acid buffer containing 0.15 mol/L sodium chloride
Fluorescence analysis conditions: excitation wavelength: 365 nm, fluorescence wavelength: 447 nm FIG. 4 shows an HPLC analysis chart of the analysis samples of the test groups 1 to 3 to which the sample was attached for five hours. Table 4 shows the average value of the peak areas of the analysis samples of each test group obtained after the cotton lint was attached for a specific period of time.

As a result of HPLC analysis, it was confirmed that the fluorescence intensity in the skin significantly increased in the analysis samples in the test group 1. On the other hand, no significant difference was observed for the test group 2.

TABLE 4

| | Attachment time | Average value of peak areas (mV · s) | Standard error |
|---|---|---|---|
| Test group 1 | 1 hour | 1,120,686 | 163,810 |
| | 3 hours | 1,365,707 | 89,110 |
| | 5 hours | 1,313,111 | 180,705 |
| Test group 2 | 1 hour | 356,634 | 46,969 |
| | 3 hours | 248,832 | 17,819 |
| | 5 hours | 214,389 | 35,097 |
| Test group 3 | 1 hour | 510,210 | 105,779 |
| | 3 hours | 279,141 | 22,033 |
| | 5 hours | 306,915 | 18,779 |

5.5.1-6. Determination of Low-Molecular-Weight Hyaluronic Acid Absorbed into Skin The hyaluronic acid percutaneous absorption was calculated for the test groups 1 to 3 from the fluorescence peak area in the analysis sample shown in Table 4. Since the peak was also detected in the test group 3 (control group), the average value of the peak areas of the test group 3 was subtracted from the fluorescence peak area of the analysis sample in order to eliminate the effects. It is considered that the peak was also detected in the test group 3 due to a fluorescent substance (e.g., vitamin, aromatic amino acid, and cholesterol) originally contained in the living body. Taking into account the difference in the amount of skin collected from each analysis sample, the hyaluronic acid percutaneous absorption was calculated by the following expression 6 using a value obtained by dividing the peak area by the weight of the skin sample.

$$\text{Weight of hyaluronic acid absorbed per } g \text{ of skin } (g) = \\ [\text{peak area of sample/skin sampling weight } (g) - \\ \text{sigma (peak area of control/skin sampling weight } (g))/ \\ n \text{ (number of samples per group)}] \times (\text{peak area of STD solution/} \\ \text{peak area of STD solution} \times 100) \times \\ \text{amount of sample solution } (g) \quad (6)$$

A 1% aqueous solution of the sample used for the test was 100-fold diluted and used as a standard (STD) solution. The STD solution was analyzed by HPLC to determine the peak area.

Figure 5:
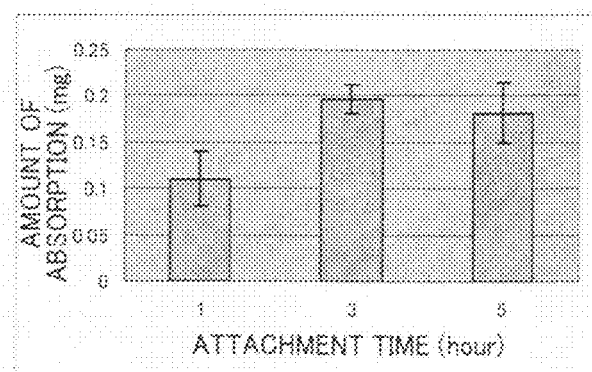
FIG. 5 is a graph showing the relationship between the attachment time of a sample in a test group 1 and an increase in the amount of hyaluronic acid per g of a skin in an analysis sample of the test group 1 determined by Test Example 1.

FIG. 5 shows the relationship between the sample attachment time of the test group 1 and an increase in the amount of hyaluronic acid per g of the skin of the analysis sample of the test group 1. As shown in FIG. 5, the amount of percutaneous absorption of the hyaluronic acid increased with time when the sample attachment time was 1 to 3 hours, and almost reached equilibrium when the sample attachment time was 3 to 5 hours. Specifically, the test group 1 (i.e., the group to which the low-molecular-weight hyaluronic acid was applied) showed a significant increase in fluorescence peak as compared with the control group (i.e., the test group 3) when the sample attachment time was 1, 3, and 5 hours.

On the other hand, no significant difference was observed for the test group 2 as compared with the test group 3 (i.e., an increase in hyaluronic acid per g of the skin was almost zero). This suggests that hyaluronic acid was percutaneously absorbed into the test group 2 to only a small extent. Hyaluronic acid was not absorbed into the skin homogenized liquid of the test group 2. This indicates that the skin was sufficiently washed after the sample was attached.

Specifically, while the low-molecular-weight hyaluronic acid according to the invention was absorbed into the skin through the surface of the skin, the hyaluronic acid used for the test group 2 remained on the surface of the skin without being absorbed into the skin due to a high molecular weight (1,800,000).

5.5.1-7. Confirmation Test

Figure 6:
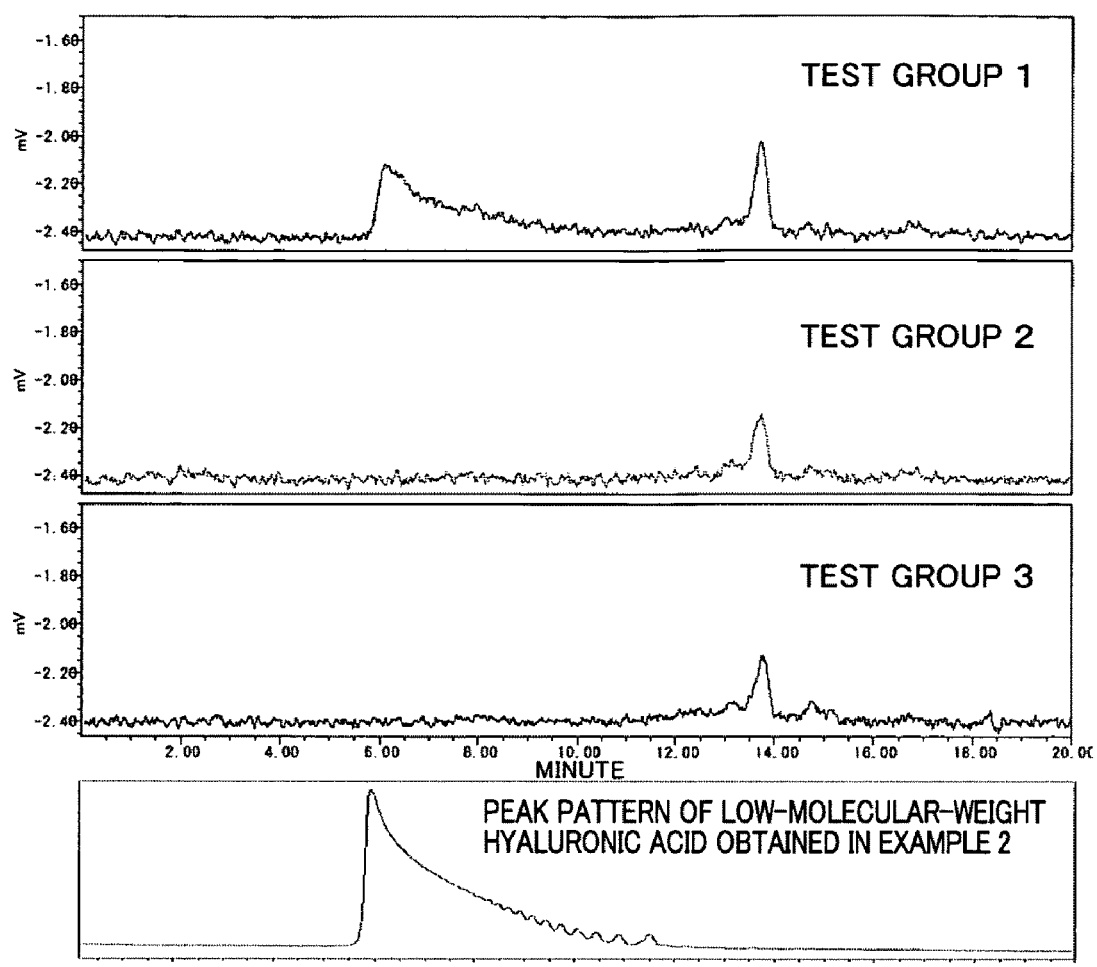
FIG. 6 shows an HPLC analysis chart of each analysis sample in test groups 1 to 3 and a low-molecular-weight hyaluronic acid obtained in Example 2 determined by low-molecular-weight column chromatography analysis conducted as a confirmation test in Test Example 1.

The analysis sample (supernatant liquid) obtained by the above-described test method was subjected to low-molecular-weight column chromatography analysis. The detected fluorescence peak was attributed to a fluorescent substance originating from the fluorescent hyaluronic acid or the skin instead of an unreacted fluorescence-labeling substance (DMEQ-hydrazide). FIG. 6 shows an HPLC analysis chart of each analysis sample subjected to low-molecular-weight column chromatography analysis. The low-molecular-weight column chromatography analysis conditions were as follows.
Analyzer: HPLC (Waters 2690+470)
Column: YMC-Pack Diol 120 (gel filtration column)
Column temperature: room temperature
Flow rate: 1 mL/min
Injection amount: 20 microliters
Mobile phase: 0.003 mol/L phosphoric acid buffer (containing 0.15mol/L sodium chloride)
Fluorescence analysis conditions: excitation wavelength: 365 nm, fluorescence wavelength: 447 nm

5.6. Test Example 2

In this test example, the low-molecular-weight hyaluronic acid according to the invention was percutaneously administered to a human subject to evaluate the percutaneous absorbability of the low-molecular-weight hyaluronic acid. Specifically, gauze provided with the low-molecular-weight hyaluronic acid according to the invention was attached to the forearm of the subject for eight hours per day over three days (8 hours/day×3 days). The skin moisture content was measured and compared with the skin moisture content when gauze provided with the control (distilled water) was attached.

5.6.1. Sample

Sample I: 1% aqueous solution of low-molecular-weight hyaluronic acid obtained in Example 2
Sample II: 1% aqueous solution of hyaluronic acid having a molecular weight of 1,400,000 ("Hyaluronsan HA-LQ" manufactured by Q.P. Corporation)
Sample III: distilled water

5.6.2. Measurement Instrument

Moisture meter: "SKICON-200" manufactured by I.B.S. Co., Ltd.

5.6.3. Measurement Method

Pieces of gauze (area: 3×3 cm$^2$) respectively provided with 1 mL of the samples I to III were attached to the forearm of each subject (fifteen 25 to 50-year-old subjects) for 48 hours. After removing the gauze, the skin moisture content in the portion to which the gauze was attached was measured using the moisture meter. The moisture content was measured immediately before attachment, immediately after attachment, when one day elapsed after attachment, and when four days elapsed after attachment. The results are shown in Table 5. Each value shown in Table 5 indicates the average value for five subjects.

TABLE 5

| | Moisture content [microS] | | | |
|---|---|---|---|---|
| | Before attachment | Immediately after attachment | When one day elapsed after attachment | When four days elapsed after attachment |
| Sample I | 7 | 54 | 38 | 15 |
| Sample II | 10 | 6 | 11 | 10 |
| Sample III | 5 | 8 | 4 | 6 |

As shown in Table 5, when the sample I was attached, the skin moisture content could be maintained sufficiently and continuously as compared with the case of attaching the sample II or III. In particular, the skin moisture content could be maintained continuously after removal of the gauze as compared with the case of attaching the sample II or III.

5.7. Test Example 3

In this test example, toilet lotion containing the low-molecular-weight HA obtained in each of Examples 1 to 3 (100 mL, contained in a plastic container) was prepared as a cosmetic preparation according to the following formulation.

| | |
|---|---|
| Cetyl octanoate | 0.30% |
| Octyl methoxycinnamate | 0.15% |
| Tocopherol acetate | 0.10% |
| Emalex RWIS-158 (isostearic acid PEG-58 hydrogenated castor oil) | 2.00% |
| Eldew PS-306 (lauroyl glutamic acid di(octyldodecyl/phytosteryl/behenyl)) | 0.50% |
| Butylparaben | 0.10% |
| Methylparaben | 0.20% |
| 1,3-Butylene glycol | 5.00% |
| Low-molecular-weight hyaluronic acid | 0.02% |
| Water | 91.63% |
| Total | 100.00% |

In this test example, toilet lotion that advantageously maintained the skin moisture content could be obtained by incorporating the low-molecular-weight HA obtained in each of Examples 1 to 3.

5.8. Test Example 4

In this test example, toilet lotion containing the low-molecular-weight HA obtained in each of Examples 1 to 3 (100 mL, contained in a plastic container) was prepared as a cosmetic preparation according to the following formulation.

| | |
|---|---|
| Dimethicone | 2.00% |
| Cyclomethicone | 21.00% |
| Jojoba oil | 0.10% |
| Emalex SS-1906EX (PEG-10 dimethicone) | 4.00% |
| Dimethylsilylsilica | 0.20% |
| Pemulen TR-2 ((acrylic acid/alkyl acrylate (C10-30)) copolymer) | 0.05% |
| Tocopherol acetate | 0.10% |
| Propylparaben | 0.05% |
| Butylparaben | 0.05% |
| Methylparaben | 0.10% |
| Iron oxide | 0.00% |
| 1,3-Butylene glycol | 1.00% |
| Low-molecular-weight hyaluronic acid | 0.05% |
| Glycerol | 25.00% |
| Magnesium sulfate | 0.20% |
| Water | 46.10% |
| Total | 100.00% |

In this test example, toilet lotion that advantageously maintained the skin moisture content could be obtained by incorporating the low-molecular-weight HA obtained in each of Examples 1 to 3.

5.9. Test Example 5

In this test example, milky lotion containing the low-molecular-weight HA obtained in each of Examples 1 to 3 (100 mL, contained in a plastic container) was prepared as a cosmetic preparation according to the following formulation.

| | |
|---|---|
| Propylene glycol | 7.92% |
| Trehalose | 0.03% |
| Low-molecular-weight hyaluronic acid | 0.01% |
| Mineral oil | 3.00% |
| Trioctanoin | 1.50% |
| Squalene | 1.00% |
| Stearic acid | 0.50% |
| Cetearyl alcohol | 0.50% |
| Lanolin | 0.30% |
| Paraffin | 0.20% |
| Sorbitan stearate | 1.40% |
| Tetra oleate Solbase-30 | 1.00% |
| Polysorbate 60 | 0.80% |
| Methylparaben | 0.20% |
| Propylparaben | 0.10% |
| Ethanol | 0.01% |
| Phenoxyethanol | suitable quantity |
| Carbomer | 0.10% |
| Potassium hydroxide | 0.10% |
| BHT | 0.02% |
| Tocopherol | suitable quantity |
| EDTA-2 sodium | 0.02% |
| Water | balance |

In this test example, milky lotion that advantageously maintained the skin moisture content could be obtained by incorporating the low-molecular-weight HA obtained in each of Examples 1 to 3.

5.10. Test Example 6

In this test example, cream containing the low-molecular-weight HA obtained in each of Examples 1 to 3 (50 g, contained in a plastic container with a screw cap) was prepared as a cosmetic preparation according to the following formulation.

| | |
|---|---|
| Squalene | 11.00% |
| Dimethicone | 1.00% |
| Behenyl alcohol | 3.00% |
| Lauroyl glutamate dioctyl dodecyl | 2.00% |
| Emalex GMS-50 (glyceryl stearate (SE)) | 8.00% |
| Emalex 805 (PEG-5 stearate) | 2.00% |
| Propylparaben | 0.10% |
| Propylene glycol | 5.00% |
| Methylparaben | 0.20% |
| Urea | 5.00% |
| Low-molecular-weight hyaluronic acid | 0.03% |
| Water | 62.67% |
| Total | 100.00% |

In this test example, cream that advantageously maintained the skin moisture content could be obtained by incorporating the low-molecular-weight HA obtained in each of Examples 1 to 3.

5.11. Test Example 7

In this test example, cleansing cream containing the low-molecular-weight HA obtained in each of Examples 1 to 3 (50 g, contained in a plastic container with a screw cap) was prepared as a cosmetic preparation according to the following formulation.

| | |
|---|---|
| Mineral oil | 30.00% |
| Paraffin | 3.00% |
| Beeswax | 2.00% |
| Cetyl octanoate | 25.00% |
| Behenyl alcohol | 5.00% |
| Glyceryl stearate | 1.00% |
| Emalex 600di-ISEX (PEG-12 diisostearate) | 3.00% |
| Emalex 620 (Steareth-20) | 1.00% |
| Tocopherol acetate | 0.10% |
| Propylparaben | 0.15% |
| Stearoyl NA glutamate | 0.40% |
| 1,3-Butylene glycol | 3.00% |
| Methylparaben | 0.15% |
| Xanthan gum | 10.00% |
| Low-molecular-weight hyaluronic acid | 0.10% |
| Water | 16.10% |
| Total | 100.00% |

In this test example, cleansing cream that advantageously maintained the skin moisture content could be obtained by incorporating the low-molecular-weight HA obtained in each of Examples 1 to 3.

5.12. Test Example 8

In this test example, makeup base containing the low-molecular-weight HA obtained in each of Examples 1 to 3 (30 g, contained in a covered plastic container) was prepared as a cosmetic preparation according to the following formulation.

| | |
|---|---|
| Ethanol | 10.00% |
| Menthol | 0.02% |
| Glycerol | 5.00% |
| BG | 3.00% |
| Low-molecular-weight hyaluronic acid | 0.01% |
| Dimethicone | 2.00% |
| Trioctanoin | 2.00% |
| Dimethyl PABA octyl | 0.50% |
| Oxybenzone | 0.05% |
| Carbomer | 0.30% |
| Silica | 0.20% |
| AMP | 0.20% |
| Methylparaben | 0.16% |
| Phenoxyethanol | suitable quantity |
| Tocopherol | 0.02% |
| EDTA-2 sodium | 0.01% |
| Water | balance |

In this test example, makeup base that advantageously maintained the skin moisture content could be obtained by incorporating the low-molecular-weight HA obtained in each of Examples 1 to 3.

5.13. Test Example 9

In this test example, hair conditioner containing the low-molecular-weight HA obtained in each of Examples 1 to 3 (500 mL, contained in a plastic container) was prepared as a cosmetic preparation according to the following formulation.

| | |
|---|---|
| Dimethicone | 3.00% |
| Propylene glycol | 8.00% |
| Mineral oil | 2.00% |
| Glycerol | 3.00% |
| PPG-30 | 0.50% |
| Steareth-4 | 1.00% |
| Cetrimonium bromide | 2.00% |
| Cetanol | 2.00% |
| Low-molecular-weight hyaluronic acid | 0.50% |
| Hydrolyzed collagen | 1.00% |
| Hydrolyzed silk | 1.00% |
| Behentrimonium methosulfate | 0.80% |
| Phenoxyethanol | 0.40% |
| Cetostearyl alcohol | 0.50% |
| Stearyl alcohol | 0.50% |
| EDTA-2 sodium | 0.10% |
| Methylparaben | 0.10% |
| Essence | suitable quantity |
| Water | 73.60% |
| Total | 100.00% |

In this test example, hair conditioner that advantageously maintained the skin moisture content could be obtained by incorporating the low-molecular-weight HA obtained in each of Examples 1 to 3.

5.14. Test Example 10

In this test example, after-sun lotion containing the low-molecular-weight HA obtained in each of Examples 1 to 3 (100 mL, contained in a plastic container) was prepared as a cosmetic preparation according to the following formulation.

| | |
|---|---|
| Ethanol | 11.04% |
| BG | 4.16% |
| *Scutellaria* root extract | suitable quantity |
| Low-molecular-weight hyaluronic acid | 0.50% |
| Stearyl alcohol | 0.72% |
| Avocado oil | 0.72% |
| Stearic acid | 0.02% |
| Orizanol | suitable quantity |
| Polysorbate | 0.23% |
| PPG-6 decyltetradeses-20 | 0.20% |
| Octoxynol-3 | 0.08% |
| Methylparaben | 0.14% |
| Propylparaben | 0.07% |
| Carbomer | 0.13% |
| PVP | suitable quantity |
| Potassium hydroxide | 0.04% |
| EDTA-2 sodium | 0.01% |
| Tocopherol | suitable quantity |
| Water | 75.10% |
| Total | 100.00% |

In this test example, after-sun lotion that advantageously maintained the skin moisture content could be obtained by incorporating the low-molecular-weight HA obtained in each of Examples 1 to 3.

5.15. Test Example 11

In this test example, after-shave lotion containing the low-molecular-weight HA obtained in each of Examples 1 to 3 (100 mL, contained in a plastic container) was prepared as a cosmetic preparation according to the following formulation.

| | |
|---|---|
| Ethanol | 58.00% |
| Menthol | 0.10% |
| Propylene glycol | 2.00% |
| Glycyrrhizinate dipotassium | 0.05% |
| Low-molecular-weight hyaluronic acid | 2.00% |
| Essence | 0.10% |
| Water | balance |

In this test example, after-shave lotion that advantageously maintained the skin moisture content could be obtained by incorporating the low-molecular-weight HA obtained in each of Examples 1 to 3.

5.16. Test Example 12

In this test example, bath agent containing the low-molecular-weight HA obtained in each of Examples 1 to 3 (200 mL, contained in a plastic container) was prepared as a cosmetic preparation according to the following formulation.

| | |
|---|---|
| Cetyl octanoate | 43.80% |
| Octoxynol-10 | 8.00% |
| Butylparaben | 0.20% |
| Methylparaben | 0.10% |
| Glycerol | 2.00% |
| Low-molecular-weight hyaluronic acid | 1.00% |
| Water | 44.90% |
| Total | 100.00% |

In this test example, bath oil that advantageously maintained the skin moisture content could be obtained by incorporating the low-molecular-weight HA obtained in each of Examples 1 to 3.

5.17. Test Example 13

In this test example, a warm cataplasm containing the low-molecular-weight HA obtained in each of Examples 1 to 3 was prepared as a pharmaceutical composition according to the following formulation.

| | |
|---|---|
| Sodium polyacrylate | 4.00 g |
| Carboxymethylcellulose sodium | 2.00 g |
| Kaolin | 5.00 g |
| Gelatin | 3.00 g |
| Glycerol | 20.00 g |
| Capsicum extract | 0.15 g |
| Low-molecular-weight hyaluronic acid | 5.00 g |
| Water | 60.85 g |
| Total | 100.00 g |

In this test example, a warm cataplasm that advantageously maintained the skin moisture content could be obtained by incorporating the low-molecular-weight HA obtained in each of Examples 1 to 3.

5.18. Test Example 14

In this test example, a cold percutaneous absorption type cataplasm containing the low-molecular-weight HA obtained in each of Examples 1 to 3 was prepared as a pharmaceutical composition according to the following formulation.

| | |
|---|---|
| Low-molecular-weight hyaluronic acid | 2.50 g |
| Indometacin | 0.30 g |
| L-menthol | 0.40 g |
| Sodium polyacrylate | 6.50 g |
| Carboxymethylcellulose sodium | 1.00 g |
| Gelatin | 3.00 g |
| Glycerol | 29.70 g |
| Aluminum glycinate | 0.08 g |
| Polyoxyethylene hydrogenated castor oil | 0.50 g |
| Lactic acid | 1.00 g |
| Water | 55.02 g |
| Total | 100.00 g |

In this test example, a cold percutaneous absorption type cataplasm that advantageously maintained the skin moisture content could be obtained by incorporating the low-molecular-weight HA obtained in each of Examples 1 to 3.

5.19. Test Example 15

In this test example, a grapefruit jelly beverage contained in a spout pouch containing the low-molecular-weight HA obtained in each of Examples 1 to 3 (contained in a transparent spout pouch (100 g)) was prepared as a food composition according to the following formulation.

| | |
|---|---|
| Low-molecular-weight hyaluronic acid | 0.1 g |
| 5-fold concentrated grapefruit fruit juice | 2.0 g |
| Carrageenan (gelling agent) | 1.0 g |
| Xanthan gum (thickener) | 0.5 g |
| Sucralose (sweetener) | 0.1 g |
| Citric acid | 1.0 g |
| Sodium citrate | 0.2 g |
| Grapefruit essence | 0.5 g |
| Purified water | 94.6 g |
| Total | 100.00 g |

In this test example, a grapefruit jelly beverage exhibiting an excellent flavor and texture could be obtained by incorporating the low-molecular-weight HA obtained in each of Examples 1 to 3.

The invention claimed is:

1. A low-molecular-weight hyaluronic acid and/or its salt having an average molecular weight of 5000 to 20,000, the low-molecular-weight hyaluronic acid and/or its salt having a molecular weight distribution in which the proportion of components having a molecular weight of 10,000 or less is 40 wt % or more and the proportion of components having a molecular weight of 50,000 or more is in the range of 0.2 wt % or more to 5 wt % or less.

2. The low-molecular-weight hyaluronic acid and/or its salt according to claim 1,
wherein the low-molecular-weight hyaluronic acid and/or its salt has a molecular weight distribution in which the proportion of components having a molecular weight of 10,000 or less is 40 wt % or more and the proportion of components having a molecular weight of 50,000 or more is in the range of 0.2 wt % or more to 1 wt % or less.

3. The low-molecular-weight hyaluronic acid and/or its salt according to claim 2,
wherein the proportion of components having a molecular weight of 10,000 or less is 50 wt % or more.

4. The low-molecular-weight hyaluronic acid and/or its salt according to claim 1, the low-molecular-weight hyaluronic acid and/or its salt being produced by dispersing hyaluronic acid and/or its salt in an acidic aqueous medium.

5. The low-molecular-weight hyaluronic acid and/or its salt according to claim 1, the low-molecular-weight hyaluronic acid and/or its salt being produced by dispersing hyaluronic acid and/or its salt in an aqueous medium having a pH of 2 or less with heating, and drying by heating a residue obtained by removing the aqueous medium from the dispersion.

6. The low-molecular-weight hyaluronic acid and/or its salt according to claim 1, wherein a 1 wt % aqueous solution of the low-molecular-weight hyaluronic acid and/or its salt has a kinematic viscosity of 2 mm$^2$/s or less.

7. The low-molecular-weight hyaluronic acid and/or its salt according to claim 1, wherein the absorbance ($A_{660}$) of a liquid obtained by adding a 0.5 g/mL cetylpyridinium chloride aqueous solution (0.05 g) to a 0.1 g/mL aqueous solution (10 mL) of the low-molecular-weight hyaluronic acid and/or its salt is 0.4 Abs or more.

8. The low-molecular-weight hyaluronic acid and/or its salt according to claim 1, the low-molecular-weight hyaluronic acid and/or its salt having a sodium chloride content of 0.5% or less.

9. A cosmetic preparation comprising the low-molecular-weight hyaluronic acid and/or its salt according to claim 1.

10. A pharmaceutical composition comprising the low-molecular-weight hyaluronic acid and/or its salt according to claim 1.

11. A food composition comprising the low-molecular-weight hyaluronic acid and/or its salt according to claim 1.

12. The low-molecular-weight hyaluronic acid and/or its salt according to claim 1, the low-molecular-weight hyaluronic acid and/or its salt being white powder.

* * * * *